US00PP32533P3

(12) United States Plant Patent
Castellarin et al.

(10) Patent No.: US PP32,533 P3
(45) Date of Patent: Dec. 1, 2020

(54) GRAPEVINE PLANT NAMED 'PINOT ISKRA'

(50) Latin Name: ***Vitis vinifera* L.**
Varietal Denomination: PINOT ISKRA

(71) Applicants: UNIVERSITÀ DEGLI STUDI DI UDINE, Udine (IT); INSTITUTO DI GENOMICA APPLICATA, Udine (IT)

(72) Inventors: Simone Diego Castellarin, Vancouver (CA); Guido Cipriani, Faedis (IT); Gabriele Di Gaspero, Cividale del Friuli (IT); Michele Morgante, Tricesimo (IT); Enrico Peterlunger, Codroipo (IT); Raffaele Testolin, Udine (IT)

(73) Assignees: UNIVERSITÀ DEGLI STUDI DI UDINE, Udine (IT); INSTITUTO DI GENOMICA APPLICATA, Udine (IT)

( * ) Notice: Subject to any disclaimer, the term of this patent is extended or adjusted under 35 U.S.C. 154(b) by 0 days.

(21) Appl. No.: 16/602,637

(22) Filed: Nov. 12, 2019

(65) Prior Publication Data

US 2020/0205331 P1 Jun. 25, 2020

(30) Foreign Application Priority Data

Dec. 20, 2018 (QZ) ..... PBR 20183516

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./205, 207
See application file for complete search history.

*Primary Examiner* — Susan McCormick Ewoldt
(74) *Attorney, Agent, or Firm* — Klarquist Sparkman, LLP

(57) ABSTRACT

A new grape variety distinguished by its resistance to downy mildew and powdery mildew, strong blistering on the upper side of the leaf blade, early-medium harvesting time (end of August in northeastern Italy), and semi-erect shoot attitude.

4 Drawing Sheets

Latin name of the genus and species of the plant claimed: *Vitis vinifera* L.
Variety denomination: 'PINOT ISKRA'.

CROSS REFERENCE TO RELATED APPLICATIONS

This application claims the benefit of priority from QZ Community Plant Variety Office (CPVO) Application No. 20183516, filed Dec. 20, 2018.

BACKGROUND

The present application relates to a new and distinct variety of grape named 'PINOT ISKRA'. Our new plant resulted from a controlled cross and is a selection from crossing SK-00-1/7 (unpatented) as the seed parent with Pinot Blanc (unpatented) as the pollen parent in 2005. The resulting plant was selected in 2013 when growing in a cultivated area in Udine, Italy.

'PINOT ISKRA' is primarily adapted to the climate and growing conditions of the temperate regions with average yearly temperature about 13° C., minimum winter temperature about −20° C., annual rainfall around 700-1500 mm of rain (e.g., North-Eastern Italy, Friuli). This region provides the necessary year-round temperatures required for it to produce and maintain a strong vigorous plant with consistent fruit production.

SUMMARY

The 'PINOT ISKRA' variety is distinguished from other grape varieties due to the following unique combination of characteristics: resistance to downy mildew and powdery mildew, strong blistering on the upper side of the leaf blade, early-medium harvesting time (end of August in northeastern Italy), and semi-erect shoot attitude. A comparison of the new variety to its parents, *Vitis vinifera* 'Pinot blanc' (unpatented) and *Vitis* cross 'SK-00-1/7' (unpatented), is provided in Table 1.

TABLE 1

| Characteristic | 'PINOT ISKRA' | Female Parent 'SK-00-1/7' |
|---|---|---|
| vigour | Medium- high | Medium |
| growth habit | Semi-erect | Semi-erect |
| leaf | Very small to small, dark green color (upper surface) RHS N134A, very few hairs in both surfaces, pentagonal shape, medium teeth, strong blistering of upper side of blade | Medium, pentagonal shape, medium teeth, medium blistering of upper side of blade |
| cluster | low weight, cylindrical with one or two middle size wings, compact, globose berry, berry skin with yellow-green color, soft flesh, neutral taste, no flesh coloration | medium weight, cylindrical, globose berry, berry skin with yellow-green color, soft flesh, neutral taste, no flesh coloration |
| harvesting time | Early-medium [end of August (Middle Friuli, northeastern Italy)] | Medium-early [middle September (Middle Friuli, northeastern Italy)] |

TABLE 1-continued

| | | |
|---|---|---|
| resistances | Resistant to downy mildew and to powdery mildew | Resistant to downy mildew, resistant to powdery mildew |
| | Characteristic | Male Parent Pinot blanc |
| | vigour | Medium |
| | growth habit | Horizontal |
| | leaf | Medium, dark green color (upper surface) RHS N134A, very few hairs in both surfaces, pentagonal shape, small teeth, medium blistering of upper side of blade |
| | cluster | low weight, cylindrical with one or two wings, compact, broad ellipsoid berry, berry skin with yellow-green color, soft flesh, neutral taste, no flesh coloration |
| | harvesting time | Medium [early September (Middle Friuli, northeastern Italy)] |
| | resistances | No resistance to downy mildew or to powdery mildew |

Of the many commercial cultivars known to the inventor, the most similar to the new grapevine 'PINOT ISKRA' is the male parent 'Pinot blanc', to which a comparison has been provided above.

Asexual reproduction of this new variety by grafting onto K5BB rootstock was first performed in February 2014 in Rauscedo, Friuli Venezia Giulia Region, Italy, and has demonstrated that that the foregoing characteristics for the new cultivar come true to form, are firmly fixed, and are established and transmitted through succeeding propagations. The new cultivar reproduces true to type.

Certain characteristics of this variety may change with changing environmental conditions (such as photoperiod, temperature, moisture, soil conditions, nutrient availability, or other factors). Color descriptions and other terminology are used in accordance with their ordinary dictionary descriptions, unless the context clearly indicates otherwise. Color designations (hue/value/chroma) are made with reference to The Royal Horticultural Society (R.H.S.) Colour Chart, 5$^{th}$ edition, London, England, 2007.

Figure 1:
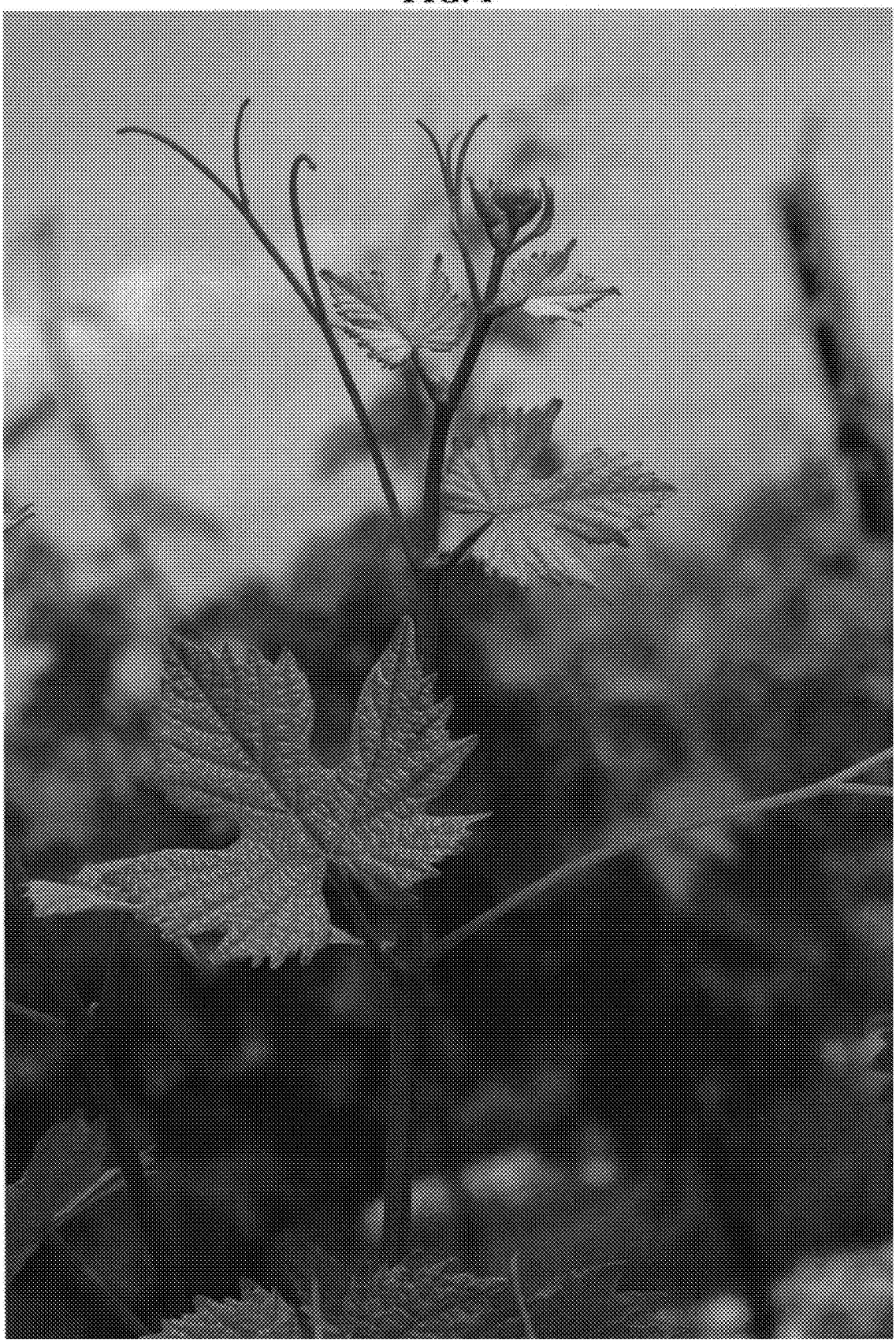
FIG. 1 is a photograph showing a shoot a leaf of the new variety 'Pinot Iskra' taken on May 24, 2017, in Rauscedo, Italy.
Figure 2:
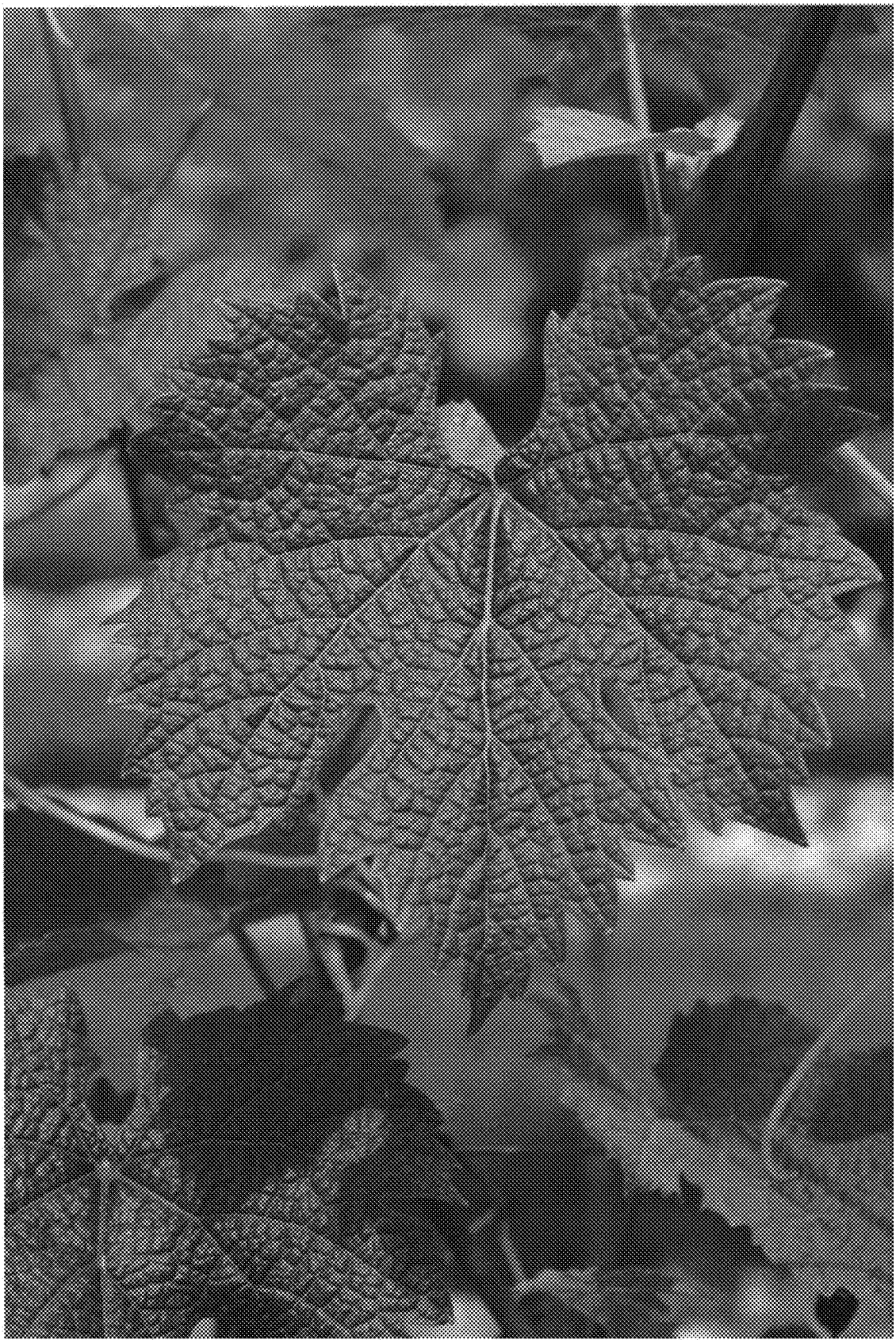
FIG. 2 is a photograph showing a leaf of the new variety 'Pinot Iskra' taken on May 24, 2017, in Rauscedo, Italy.
Figure 3:
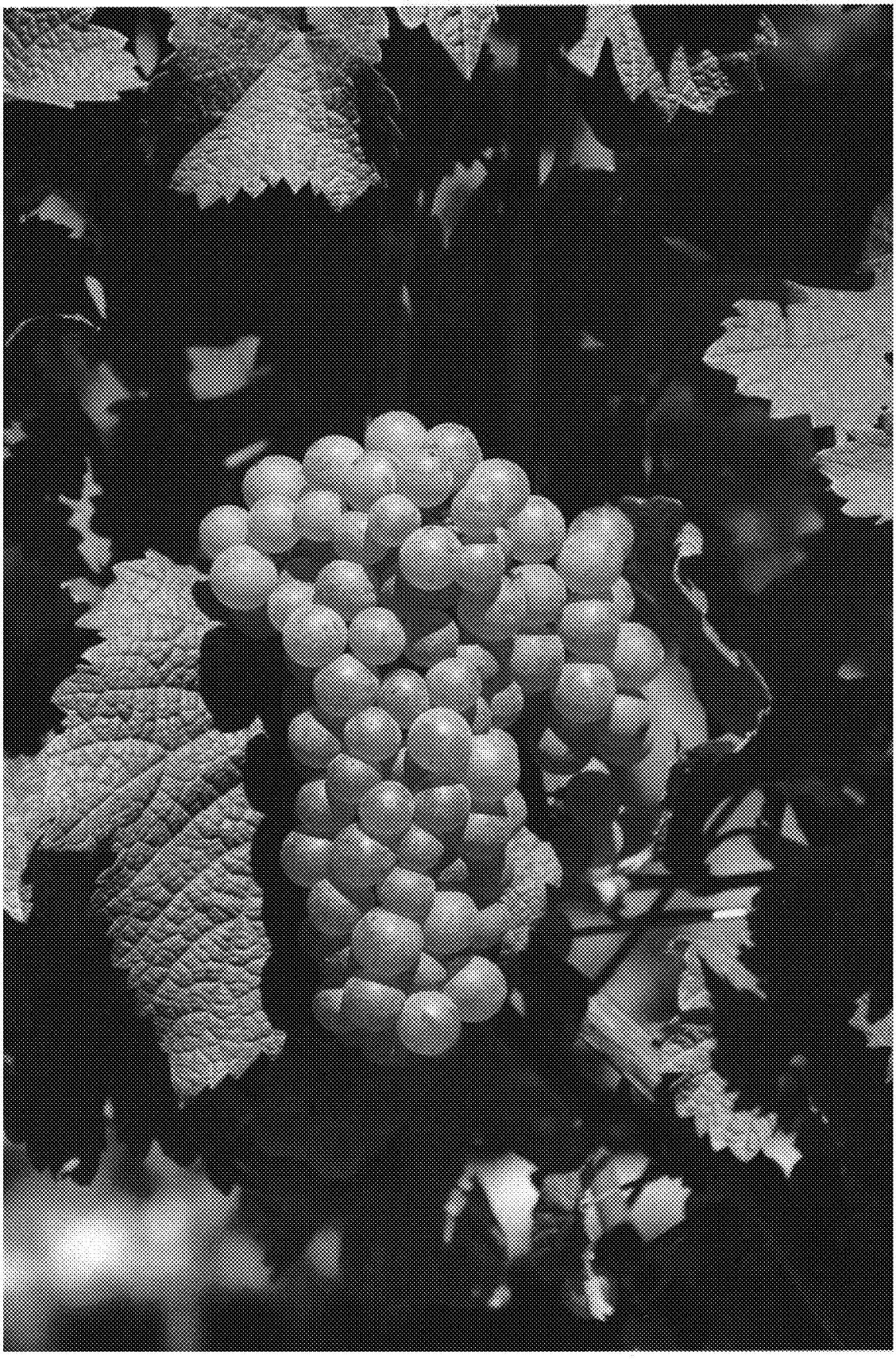
FIG. 3 is a photograph showing fruit of the new variety 'Pinot Iskra' taken on Aug. 24, 2016, in Rauscedo, Italy.
Figure 4:
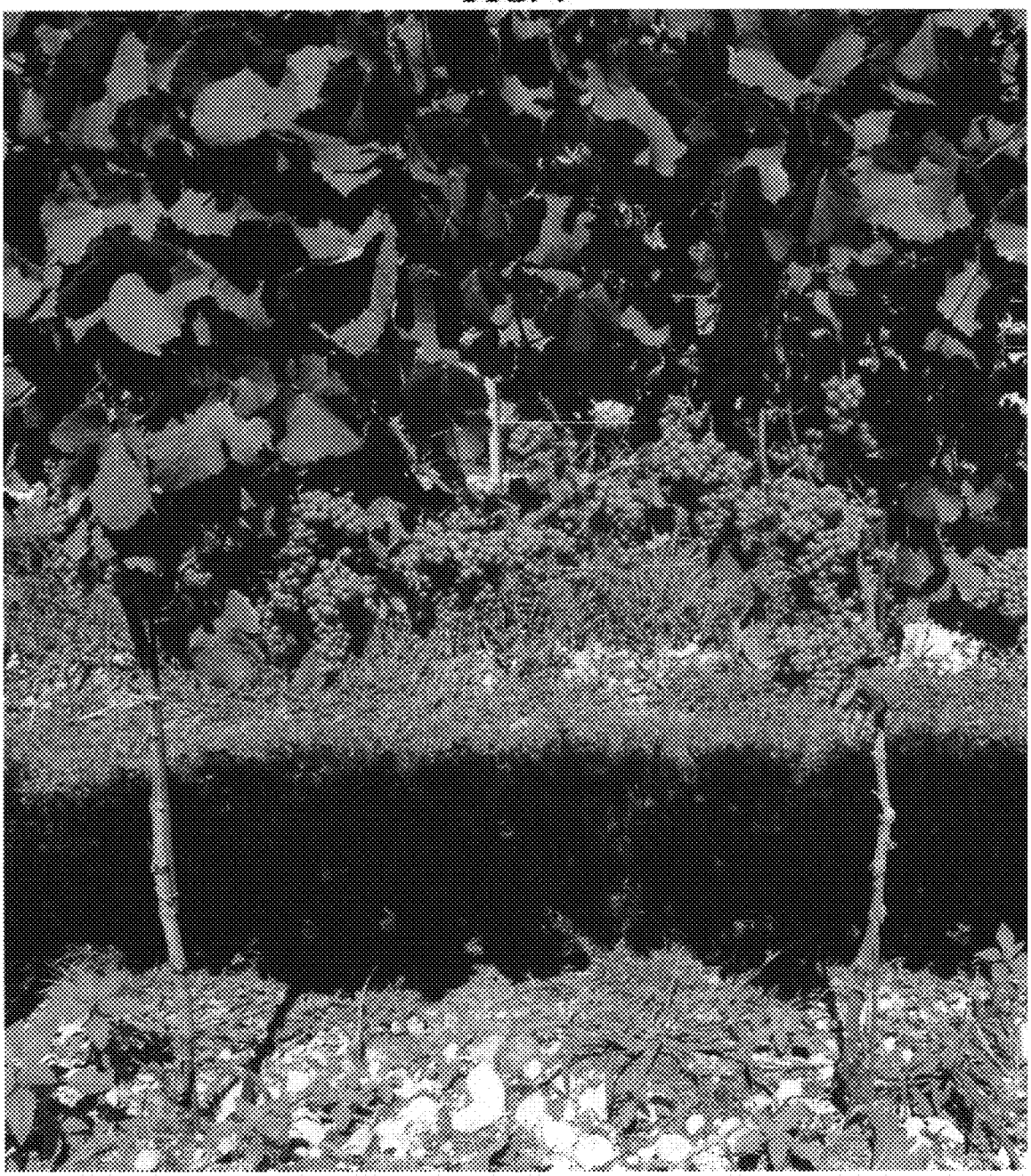
FIG. 4 is a photograph showing a plant of the new variety 'Pinot Iskra' taken on Aug. 24, 2016, in Rauscedo, Italy.

The color photograph shows typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

Botanical

The following detailed description of the 'PINOT ISKRA' variety is based on observations of asexually reproduced progeny. The observed progeny are plants which were 3-5 years of age. The following detailed description concerns the plants growing in an open field taken in Rauscedo, Italy in 2016-2018. The original plant and progeny have been observed growing in a cultivated area in Rauscedo, Italy, with medium texture soil that is rich in skeleton and alluvial in nature. Temperatures in Rauscedo, Italy range from a high of 29° C. to a low of −2° C. Average rainfall is 822 mm per year, with an average rainfall during the growing season (April-September) of 453 mm.

The chart used in the identification of colors described herein is The R.H.S. Colour Chart, 5$^{th}$ edition, except where general color terms of ordinary significance are used. The color values were determined in August-September 2018 under natural light conditions in Rauscedo, Italy.

Scientific name: *Vitis vinifera* L.

Parentage:

*Seed parent.*—Sk-00-1/7.

*Pollen parent.*—Pinot Blanc.

Plant:

*Vigor.*—Medium-high.

*Growth habit.*—Horizontal.

Trunk:

*Diameter at 50 cm.*—29 mm (6 yr-old plants).

*Bark texture.*—Ribbed.

*Bark coloration.*—N187A.

Mature cane:

*Diameter.*—9 mm.

*Bark texture.*—Ribbed.

*Bark coloration.*—RHS 179D.

Shoot:

*Opening of the shoot tip.*—Fully open for young shoot.

*Distribution of the anthocyanin coloration of the prostrate hairs of the shoot tip.*—On the margin.

*Density of prostate hair on the shoot tip.*—Low.

*Attitude (before tying).*—Semi-erect.

*Color of the dorsal side of internodes.*—Green 140B and red 53A.

*Color of the ventral side of internodes.*—Green 140B and red 53A.

*Distribution of anthocyanin coloration on the bud scales.*—Absent.

*Number of consecutive tendrils.*—2 or less.

Tendrils:

*Length.*—23.4 cm.

*Diameter.*—2 mm.

*Color.*—RHS 145C and RHS 179C.

Leaves:

*Shape*.—Pentagonal.

*Ratio length/width of teeth*.—Medium (Chasselas blanc).

*Arrangement of lobes of upper lateral sinuses*.—Slightly overlapped (Cabernet Sauvignon).

*Blistering*.—Strong blistering of upper side of blade.

*Size of blade*.—Very small to small (Gamay N; Gewurztraminer Rg); average length 97 mm; average width 131 mm.

*Young leaf*.—Color of upper surface is green RHS 134A, color of the lower surface RHS 142B and RHS N187D, with medium prostrate hairs between main veins on the lower side of blade.

*Mature leaf*.—Color of upper surface is dark green N134A, color of the lower surface RHS 140B, with sparse prostrate hairs between main veins on the lower side of blade.

*Mature leaf*.—Five lobes.

*Area of anthocyanin coloration of main veins on upper side and lower of mature blade*.—Up to the 1$^{st}$ bifurcation.

*Goffering/depressions of mature blade between the main veins*.—Medium (Trebbiano Toscano, Merlot).

*Shape of base of petiole sinus*.—Brace-shaped ({)

*Petiole sinus base limited by vein*.—Not limited.

*Petiole length compared to length of middle vein*.—Slightly longer.

*Petiole average length*.—98.8 mm.

*Petiole color* (*upper surface*).—RHS 145B and RHS 184D.

*Petiole color* (*lower surface*).—RHS 145B and RHS 185B.

*Density of prostrate hairs on petiole*.—Low.

*Density of erect hairs on petiole*.—None or very low.

*Depth of upper lateral sinuses*.—Medium; average depth of the sinus 32.6 mm.

Flower bud:

*Shape*.—Round.

*Size*.—Average.

*Color*.—Light brown.

*Bud burst*.—Beginning of April in Rauscedo, Italy.

Flowers: Fully developed stamens and fully developed gynoecium.

*Insertion of* 1$^{st}$ *inflorescence*.—3$^{rd}$ and 4$^{th}$ node.

*Number of inflorescences per shoot*.—1 to 3.

*Flowering period* (*time of beginning of flowering*).—Beginning of June in Rauscedo, Italy.

*Average flower diameter*.—2 mm.

*Inflorescence average length*.—131 mm.

*Inflorescence average width*.—90 mm.

Fruit:

*Cluster*.—Low weight (about 170 g), cylindrical with one or two middle size wings, compact.

*Time of beginning of berry ripening*.—Early.

*Berry shape*.—Globose.

*Berry length*.—About 13 mm.

*Berry width*.—About 13 mm.

*Thickness of berry skin*.—Medium-to-thick.

*Berry hilium*.—Visible.

*Color of skin* (*without bloom*).—Yellow green (154C).

*Texture*.—Soft flesh.

*Flesh color*.—RHS 150C.

*Anthocyanin coloration of flesh*.—Absent or very weak.

*Flavor*.—None/neutral.

*Berry shipping quality*.—N.a.

*Berry storage quality*.—N.a.

*Formation of seeds*.—Complete.

*Average number of seeds*.—2-3.

*Seed size*.—Medium (Pinot noir, Merlot).

*Seed color*.—Brown RHS 200C.

*Harvest time*.—Early-medium (end of August in north-eastern Italy).

*Bunch length* (*peduncle excluded*).—Short-to-medium (about 120 to 160 mm; Gewurztraminer, Muller-Thurgau).

*Bunch width*.—Narrow (about 80 mm; Riesling, Sauvignon).

*Bunch density*.—Dense.

*Length of peduncle of primary bunch*.—Short-to-medium, (about 50 to 70 mm; Gewurztraminer, Barbera).

*Color of peduncle*.—RHS 156A and RHS N200A.

*Diameter of peduncle*.—4-5 mm.

*Lignification of peduncle*.—Up to about the middle to more than the middle.

Pedicel:

*Average length*.—6-9 mm.

*Average diameter*.—1-1.5 mm.

*Color*.—RHS 145B.

Grape juice characteristics:

*Sugars* (*brix*).—20.6.

*pH*.—3.3.

*Total acidity*.—6.1 g/l.

*Tartaric acid*.—5.52 g/l.

*Malic acid*.—1.76 g/l.

Production characteristics

*Clusters per shoot*.—1.7.

*Grape production*.—3133 g/plant.

*No. of bunches/vine* (*at harvest*).—27.6.

*Average weight of the bunch*.—168 g.

*Average berry weight*.—1.53 g.

*Pruning wood weight*.—610 g/plant.

*Index of ravaz*.—5.13.

Wine produced from grapes:

*Total acidity*.—5.7 g/l.

*Tartaric acid*.—3.3 g/l.

*pH*.—3.2.

*Net extract*.—19.1 g/l.

*Alcohol*.—13.9 g/l.

*Volatile acidity*.—0.3 g/l.

*Reducing sugars*.—1.4 g/l.

TABLE 2

| Molecular Analysis | | | | | | | | | |
|---|---|---|---|---|---|---|---|---|---|
| VVS2 | | VVMD5 | | VVMD7 | | VVMD25 | | VVMD27 | |
| N + 10 | N + 28 | N + 6 | N + 10 | N + 8 | N + 26 | N + 6 | N + 14 | N + 14 | N + 14 |
| VVMD28 | | VVMD32 | | VRZAG62 | | VRZAG 79 | | | |
| N + 2 | N + 20 | N + 5 | N + 37 | N + 20 | N + 20 | N + 8 | N + 22 | | |

Use international coding based on "N" (see European project GENRES 081—A basis for the preservation and utilization of *Vitis* genetic resources)

Phenological characteristics (in Rauscedo, Italy):

*Germination*.—April 6.

*Flowering*.—June 2.

*Veraison* (*change of color*).—August 4.

*Maturation*.—August 29.

Use: Wine grape.

Disease/pest resistance: Resistance to downy mildew and powdery mildew.

We claim:

1. A new and distinct variety of *Vitis vinifera* L. plant substantially as illustrated and described herein.

* * * * *